United States Patent [19]

Wasan et al.

[11] Patent Number: 5,965,542
[45] Date of Patent: Oct. 12, 1999

[54] USE OF TEMPERATURE TO CONTROL THE SIZE OF CATIONIC LIPOSOME/PLASMID DNA COMPLEXES

[75] Inventors: Ellen K. Wasan, Vancouver; Marcel B. Bally, Bowen Island; Michael J. Hope; Dorothy L. Reimer, both of Vancouver; Quet Fah Ahkong, Surry, all of Canada

[73] Assignee: Inex Pharmaceuticals Corp., Vancouver, Canada

[21] Appl. No.: 08/816,768

[22] Filed: Mar. 18, 1997

[51] Int. Cl.$^6$ .......................... A01N 43/36; A61K 9/127; C12N 15/00; C07H 21/02
[52] U.S. Cl. .......................... 514/44; 424/450; 435/91.1; 435/91.4; 435/172.1; 435/320.1; 536/23.1
[58] Field of Search .......................... 514/44; 536/23.1; 435/89, 91.1, 91.4, 172.1, 177, 320.1; 935/52, 54; 424/450

[56] References Cited

U.S. PATENT DOCUMENTS

| | | | |
|---|---|---|---|
| 4,407,948 | 10/1983 | Goodman et al. | 435/91 |
| 5,008,050 | 4/1991 | Cullis et al. | 264/4.3 |
| 5,459,127 | 10/1995 | Felgner et al. | 514/7 |
| 5,705,385 | 1/1998 | Bally et al. | 435/320.1 |
| 5,785,992 | 7/1998 | Michial et al. | 424/450 |

FOREIGN PATENT DOCUMENTS

| | | |
|---|---|---|
| WO 93 12756 | 7/1993 | WIPO . |
| WO 93 24640 | 12/1993 | WIPO . |
| WO 96 10390 | 4/1996 | WIPO . |

OTHER PUBLICATIONS

Liu, et al., "New cationic lipid formulations for gene transfer," *Pharmaceutical Research*, 13:12:1856–1860 (1996).
Brigitte Sternberg, "Morphology of cationic liposome/DNA complexes in relation to their chemical composition," *J. Liposome Research*, 6(3):515–533 (1996).
Stamatatos, et al., "Interactions of cationic lipid vesicles with negatively charged phospholipid vesicles and biological membranes," *Biochem.*, 27(11):3917–25 (May 31, 1988).
Bertling, et al., "Use of liposomes, viral capsids, and nanoparticles as DNA carriers," *Biotech. and Applied Biochem.*, 13:390–405 (1991).
Fred D. Ledley, "Nonviral gene therapy: the promise of genes as pharmaceutical products," *Human Gene Therapy*, 6:1129–1144 (Sep. 1995).
Mahato, et al., "Physicochemical and pharmacokinetic characteristics of plasmid DNA/cationic liposome complexes," *J. Pharm. Sci.*, 84(11):1267–1271 (Nov. 1995).
Gao, et al., "Potentiation of cationic liposome–mediated gene delivery by polycations," *Biochem.*, 35:1027–1036 (1996).
Lee, et al., "Folate–targeted anionic liposome–entrapped polylysine–condensed DNA for tumor cell–specific gene transfer," 271(14):8481–8487 (Apr. 5, 1996).
Hui, et al., "The role of helper lipids in cationic liposome–mediated gene transfer," *Biophysical J.*, 71:590–599 (Aug. 1996).
Sternberg, et al., "New structures in complex formation between DNA and cationic liposomes visualized by freeze-e–fracture electron microscopy," *FEBS Letters*, 356:361–366 (1994).
Tomlinson, et al., "Controllable gene therapy pharmaceutics of non–viral gene delivery systems," *J. Controlled Release*, 39:357–372 (1996).
Kabanov, et al., "DNA complexes with polycations for the delivery of genetic material into cells," *Bioconjugate Chem.*, 6:7–20 (1995).
Xu, et al., "Mechanism of DNA release from cationic liposome/DNA complexes used in cell transfection," *Biochem.*, 35:5616–5623 (1996).

*Primary Examiner*—David M. Naff
*Attorney, Agent, or Firm*—Townsend and Townsend and Crew LLP

[57] ABSTRACT

Methods of forming cationic liposome/nucleic acid complexes in which the complexes have a mean diameter of about 200 to about 300 nm are provided. The complexes are formed by combining a first solution of preformed cationic unilamellar liposomes with a mean diameter of from 100 to 150 nm, with a second solution of nucleic acid. Each of the solutions are equilibrated prior to mixing to temperatures of from 0° C. to about 12° C., preferably about 2° C. to about 7° C. The preformed cationic liposomes are typically prepared from an unsaturated cationic lipid, for example DODAC, DOTAP, DOTMA, DODAP, DMRIE, DORI, DOSPA and combinations thereof, and a neutral lipid, for example DOPE or cholesterol. The combination of the first and second solutions is typically carried out by gentle mixing over ice for a period of time of from about 10 to about 60 minutes.

17 Claims, 12 Drawing Sheets

USE OF TEMPERATURE TO CONTROL THE SIZE OF CATIONIC LIPOSOME/PLASMID DNA COMPLEXES

FIELD OF THE INVENTION

This invention relates to methods of preparing cationic liposome/nucleic acid complexes having a controlled size. These complexes are useful for the introduction of nucleic acids into cells. The liposome/nucleic acid complexes prepared by this method are stable in vivo and are suitable as nucleic acid or antisense transfer delivery vehicles, practical for clinical use.

BACKGROUND OF THE INVENTION

Developments in recombinant deoxyribonucleic acid ("DNA") technology have opened up new avenues for medical treatment. The location and sequences of an increasing number of disease-related genes are being identified, and clinical testing of nucleic acid-based therapeutics for a variety of diseases is now underway.

Gene therapy involves the introduction of genetic material into a cell to facilitate expression of a deficient or defective protein. Missing or defective genes (sequences of DNA encoding messenger RNA which are used as templates for protein construction) which are responsible for the production of these proteins result in a class of genetic disease often referred to as 'inborn errors of metabolism'. In some cases the disease can be treated by controlling the diet, as in the case of phenylketonuria, in which the liver enzyme responsible for the conversion of phenylalanine to tyrosine is defective. Untreated, this disease can result in mental retardation.

Treatments available for most genetic diseases are not as straightforward as merely altering the diet. For example, adenosine deaminase (ADA) deficiency results from a missing or defective gene that makes the adenosine deaminase enzyme. This enzyme is essential for a healthy immune system. ADA deficiency, however, is the disease successfully treated by the first human "gene transfer" experiment conducted by Kenneth Culver in 1990 (see, Culver, GENE THERAPY: A HANDBOOK FOR PHYSICIANS, Mary-Ann Liebert, Inc. publishers, p. 33–40 (1994)).

One method of introducing nucleic acids into a cell is mechanically, using direct microinjection. However this method is only practical for transfecting eukaryotic germline cells for the production of transgenic systems. To be effective in treating a disease, a nucleic acid-based therapy must enter many cells.

Systemic gene transfer entails distributing nucleic acids to target cells and then transferring the nucleic acid across a target cell membrane intact and in a form that can function in a therapeutic manner. In vivo gene transfer is complicated by serum interactions, immune clearance, toxicity and biodistribution.

The in vivo gene transfer methods under study in the clinic consist almost entirely of viral vectors. Although viral vectors have the inherent ability to transport nucleic acids across cell membranes and some can integrate exogenous DNA into the chromosomes, they can carry only limited amounts of DNA and also pose risks. One such risk involves the random integration of viral genetic sequences into patient chromosomes, potentially damaging the genome and possibly inducing a malignant transformation. Another risk is that the viral vector may revert to a pathogenic genotype either through mutation or genetic exchange with a wild type virus.

Lipid-based vectors have also been used in gene transfer and have been formulated in one of two ways. In one method, the nucleic acid is introduced into preformed liposomes made of mixtures of cationic lipids and neutral lipids. The complexes thus formed have undefined and complicated structures and the transfection efficiency is severely reduced by the presence of serum. Preformed liposomes are commercially available as LIPOFECTIN® and LIPO-FECTAMINE®. The second method involves the formation of DNA complexes with mono- or poly-cationic lipids without the presence of a neutral lipid. These complexes are prepared in the presence of ethanol and are not stable in water. Additionally, these complexes are adversely affected by serum (see, Behr, *Acc. Chem. Res.* 26:274–78 (1993)). An example of a commercially available poly-cationic lipid is TRANSFECTAM®.

Other efforts to encapsulate DNA in lipid-based formulations have not overcome these problems (see, Szoka, et al., *Ann. Rev. Biophys. Bioeng.* 9:467 (1980); and Deamer, U.S. Pat. No. 4,515,736).

Ideally, a delivery vehicle for nucleic acid will be small enough (<300 nm) and stable enough in circulation to distribute from local injection sites or following intravenous injection. The composition will have the maximum amount of nucleic acid per particle and will be homogeneous and reproducible. The composition should also efficiently transfect the target cells.

Surprisingly, the present invention provides such compositions, methods for their preparation, and methods for the introduction of nucleic acids into cells.

SUMMARY OF THE INVENTION

The present invention provides methods of forming cationic liposome/nucleic acid complexes in which the complexes have a mean diameter of about 200 to about 300 nm. The complexes are formed by combining a first solution of preformed cationic unilamellar liposomes with a mean diameter of from 100 to 150 nm, with a second solution of nucleic acid. Each of the solutions are equilibrated prior to mixing to temperatures of from 0° C. to about 12° C., preferably about 2° C. to about 7° C.

The preformed cationic liposomes are typically prepared from an unsaturated cationic lipid, for example DODAC, DOTAP, DOTMA, DODAP, DORI, DMRIE, DOSPA and combinations thereof, and a neutral lipid, for example DOPE or cholesterol.

The combination of the first and second solutions is typically carried out by gentle mixing over ice (i.e., at temperatures of 0° C. to 10° C.) for a period of time of from about 10 to about 60 minutes.

The complexes thus formed are useful in the transfection of cells, including plant cells and mammalian cells. Accordingly, the present invention provides methods for the introduction of nucleic acids into cells, both in vivo and ex vivo.

Still further, the present invention provides cationic liposome/nucleic acid compositions which are prepared by the processes described above.

DETAILED DESCRIPTION OF THE INVENTION

CONTENTS

Figure 1:
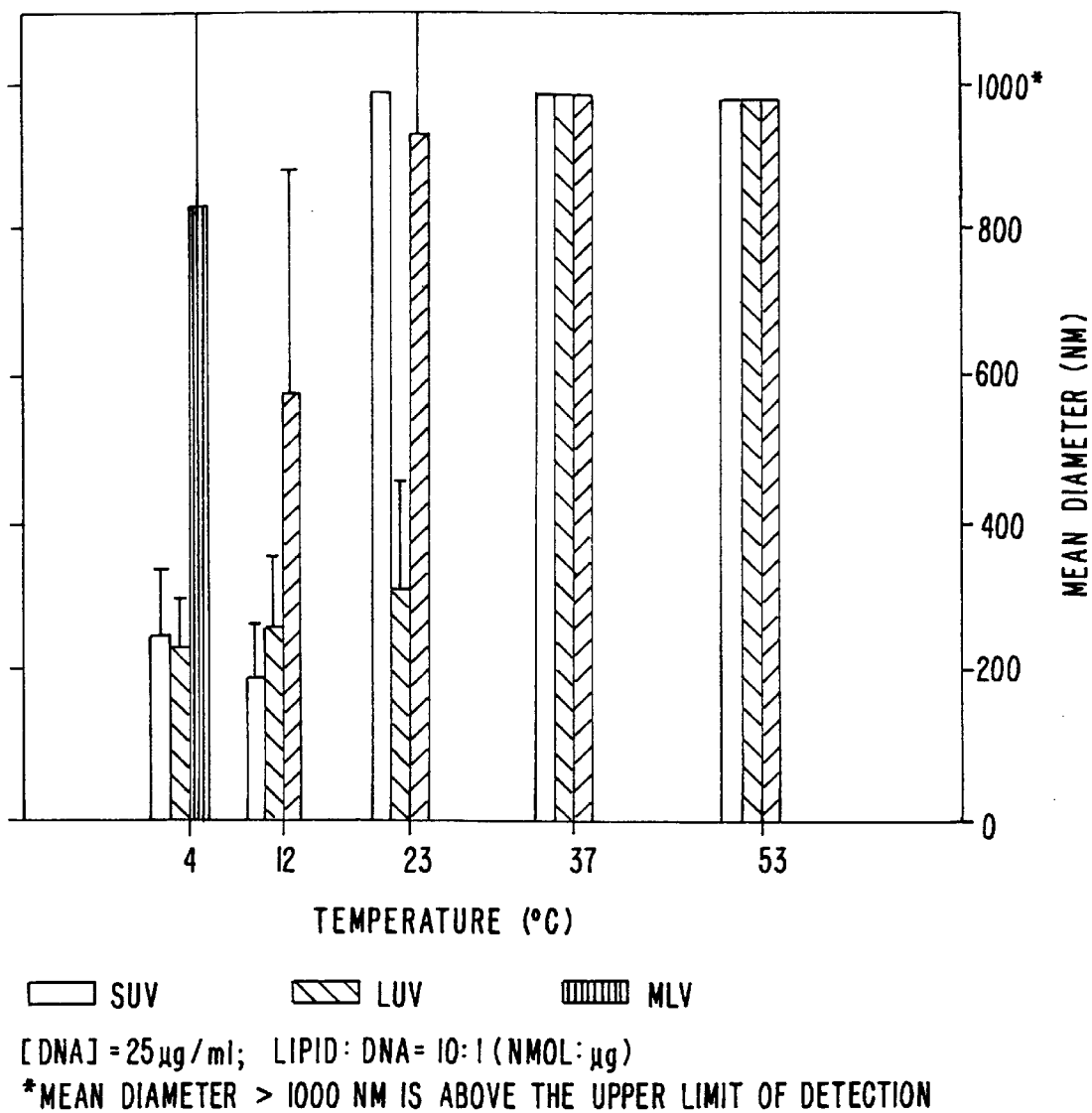
FIG. 1 illustrates the complex size control which is capable using temperature-controlled mixing.

I. Glossary
II. General
III. Methods of Preparing Cationic Liposome/Nucleic Acid Complexes
IV. Pharmaceutical Preparations
V. Methods of Transfecting Cells
VI. Examples
VII. Conclusion

I. Glossary

Abbreviations and Definitions

The following abbreviations are used herein: DC-Chol, 3β-(N-(N',N'-dimethylaminoethane)carbamoyl)cholesterol (see, Gao, et al., *Biochem. Biophys. Res. Comm.* 179:280–285 (1991)); DDAB, N,N-distearyl-N,N-dimethylammonium bromide; DMRIE, N-(1,2-dimyristyloxyprop-3-yl)-N,N-dimethyl-N-hydroxyethyl ammonium bromide; DODAC, N,N-dioleyl-N,N-dimethylammonium chloride (see commonly owned patent application U.S. Ser. No. 08/316,399, incorporated herein by reference); DODAP, 1,2-dioleoyl-3-dimethylammonium propane; DOPE, 1,2-sn-dioleoylphoshatidylethanolamine; DORI, dioleoyl derivatives of the Rosenthal inhibitor (described in U.S. Pat. No. 5,459,127, incorporated herein by reference; DOSPA, N-(1-(2,3-dioleyloxy)propyl)-N-(2-(sperminecarboxamido)ethyl)-N,N-dimethylammonium trifluoroacetate; DOTAP, N-(1-(2,3-dioleoyloxy)propyl)-N,N,N-trimethylammoniumchloride; DOTMA, N-(1-(2,3-dioleyloxy)propyl)-N,N,N-trimethylammoniumchloride; ESM, egg sphingomyelin; RT, room temperature.

As used herein, the term "pharmaceutically acceptable anion" refers to anions of organic and inorganic acids which provide non-toxic salts in pharmaceutical preparations. Examples of such anions include chloride, bromide, sulfate, phosphate, acetate, benzoate, citrate, glutamate, and lactate. The preparation of pharmaceutically acceptable salts is described in Berge, et al., *J. Pharm. Sci.* 66:1–19 (1977), incorporated herein by reference.

The term "transfection" as used herein, refers to the introduction of polyanionic materials, particularly nucleic acids, into cells. The term "lipofection" refers to the introduction of such materials using either liposome complexes or lipid particles. The polyanionic materials can be in the form of DNA or RNA which is linked to expression vectors to facilitate gene expression after entry into the cell. Thus the polyanionic material or nucleic acids used in the present invention is meant to include DNA having coding sequences for structural proteins, receptors and hormones, as well as transcriptional and translational regulatory elements (i.e., promoters, enhancers, terminators and signal sequences) and vector sequences. Methods of incorporating particular nucleic acids into expression vectors are well known to those of skill in the art, but are described in detail in, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987), both of which are incorporated herein by reference.

II. General

The present invention provides methods for preparing cationic liposome-nucleic acid complexes. The methods derive from the surprising discovery that complexes can be formed at reduced temperatures which are not aggregate complexes such as those formed at room temperature. More particularly, when mixtures of cationic unilamellar liposomes are combined with mixtures of nucleic acids at temperatures of about 2° C. to about 7° C., complexes are formed having a smaller average diameter than complexes which are formed at more elevated temperatures. The cationic liposomes used herein are those which consist essentially of unsaturated cationic lipids and DOPE.

FIG. 1 illustrates the complex size control which is possible using temperature-controlled mixing. The complexes were formed from small unilamellar vesicles (SUV), large unilamellar vesicles (LUV) and multilammelar vesicles (MLV). In each instance, the liposomes were combined with the DNA at the indicated temperature. At 37° C. and at 53° C., all formulations provides complexes with mean diameters of >1000 nm. However, at 4° C. and at 12° C., the complexes prepared from unilamellar vesicles provided complexes having mean diameters of <300 nm, while the MLVs provided complexes having mean diameters of about 800 nm and about 600 nm, respectively.

III. Methods of Forming Cationic Liposome/Nucleic Acid Complexes

In view of the above surprising discovery, the present invention provides methods of preparing cationic liposome/nucleic acid complexes comprising combining a first solution of preformed cationic liposomes with a second solution of nucleic acid, wherein each of the first and second solutions have been pre-equilibrated to temperatures of from about 0° C. to about 12° C. and wherein the preformed cationic liposomes are unilamellar and have a mean diameter of from 100 to 150 nm.

The first solution of preformed cationic liposomes is typically a mixture of unilamellar liposomes in an aqueous buffer. The term "cationic liposomes" is used herein to describe liposomes having a net positive charge. These liposomes are prepared from cationic lipids, preferably unsaturated cationic lipids and neutral lipids using standard liposome forming protocols. The term "cationic lipid" refers to any of a number of lipid species which carry a net positive charge at physiological pH. Such lipids include, but are not limited to, DODAC, DOTMA, DDAB, DOTAP, DC-Chol and DMRIE. Additionally, a number of commercial preparations of cationic lipids are available which can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega Corp., Madison, Wis., USA). As used herein, the term "unsaturated cationic lipid" refers to those lipids above which have one or more sites of unsaturation (double bond of any orientation or triple bond) in the hydrocarbon chain. Examples of such unsaturated cationic lipids include, DODAC, DODAP, DOTAP, DOSPA and DORI.

Neutral lipids used herein can be any of a number of lipid species which exist either in an uncharged or neutral zwitterionic form at physiological pH. Such lipids include, for example diacylphosphatidylcholine, diacylphosphatidylethanolamine, ceramide, sphingomyelin, cephalin, cholesterol and cerebrosides. The selection of neutral lipids for use in the cationic liposomes herein is generally guided by consideration of, e.g., liposome size and stability of the liposomes in the bloodstream. The neutral lipid component in the liposomes is a lipid having two acyl groups, (i.e., diacylphosphatidylcholine and diacylphosphatidyl-ethanolamine). Lipids having a variety of acyl chain groups of varying chain length and degree of saturation are available or may be isolated or synthesized by well-known techniques. In general, less saturated lipids are more easily sized, particularly when the liposomes must be sized below about 0.3 microns, for purposes of filter sterilization. In one group of embodiments, lipids containing saturated fatty acids with carbon chain lengths in the range of $C_{14}$ to $C_{22}$ are preferred. In another group of embodiments, lipids with mono or diunsaturated fatty acids with carbon chain lengths in the range of $C_{14}$ to $C_{22}$ are used. Additionally, lipids having mixtures of saturated and unsaturated fatty acid chains can be used. Preferably, the neutral lipids used in the present invention are DOPE, cholesterol or combinations thereof. Liposomes useful in the present invention may also be composed of sphingomyelin or phospholipids with other head groups, such as serine and inositol. Still other liposomes useful in the present invention will include small amounts of cholesterol, diglycerides, ceramides, phosphatidylethanolamine-polyoxyethylene conjugates, phosphatidic acid-polyoxyethylene conjugates, or polyethylene glycol-ceramide conjugates (e.g., PEG-Cer-$C_{14}$ or PEG-Cer-$C_{20}$).

The preformed liposomes used herein can be prepared by any of a variety of methods available for preparing unilamellar liposomes as described in, e.g., Szoka et al., *Ann. Rev. Biophys. Bioeng.* 9:467 (1980), U.S. Pat. Nos. 4,235,871, 4,501,728, 4,837,028, the text *Liposomes*, Marc J.Ostro, ed., Marcel Dekker, Inc., New York, 1983, Chapter 1, and Hope, et al., *Chem. Phys. Lip.* 40:89 (1986), all of which are incorporated herein by reference. A preferred method is described in Example 1, below.

Following liposome preparation, the liposomes may be sized to achieve a desired size range and relatively narrow distribution of liposome sizes. Preferably, the preformed liposomes used herein will be sized to a mean diameter of from about 100 to about 150 nm. Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In both methods, the size distribution can be monitored by conventional laser-beam size discrimination.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present inventions, liposomes having a size of from about 100 nm to about 150 nm are preferred, with liposomes having a size of from about 110 nm to about 130 nm being more preferred.

The first solution of cationic liposomes will typically be an aqueous solution. In preferred embodiments, the aqueous solution is a buffered solution which is used in the preparation of the liposomes. This buffer can be any biologically compatible buffer solution of, for example, isotonic saline, phosphate buffered saline, or other low ionic strength buffers.

The second solution is a solution of nucleic acids. The nucleic acids which are useful in the present invention are typically nucleotide polymers having from 10 to 100,000 nucleotide residues. Typically, the nucleic acids are to be administered to a subject for the purpose of repairing or enhancing the expression of a cellular protein. Accordingly, the nucleic acid can be an expression vector, cloning vector or the like which is often a plasmid designed to be able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in *E. coli* for cloning and construction, and in a mammalian cell for expression.

Additionally, the nucleic acid can carry a label (e.g., radioactive label, fluorescent label or colorimetric label) for the purpose of providing clinical diagnosis relating to the presence or absence of complementary nucleic acids. Accordingly, the nucleic acids, or nucleotide polymers, can be polymers of nucleic acids including genomic DNA, cDNA, mRNA or oligonucleotides containing nucleic acid analogs, for example, the antisense derivatives described in a review by Stein, et al., *Science* 261:1004–1011 (1993) and in U.S. Pat. Nos. 5,264,423 and 5,276,019, the disclosures of which are incorporated herein by reference. Still further, the nucleic acids may encode transcriptional and translational regulatory sequences including promoter sequences and enhancer sequences.

The nucleotide polymers can be single-stranded DNA or RNA, or double-stranded DNA or DNA-RNA hybrids. Examples of double-stranded DNA include structural genes, genes including control and termination regions, and self-replicating systems such as plasmid DNA. Particularly preferred nucleic acids are plasmids.

Single-stranded nucleic acids include antisense oligonucleotides (complementary to DNA and RNA), ribozymes and triplex-forming oligonucleotides. In order to increase stability, some single-stranded nucleic acids will preferably have some or all of the nucleotide linkages substituted with stable, non-phosphodiester linkages, including, for example, phosphorothioate, phosphorodithioate, phosphoroselenate, methylphosphonate, or O-alkyl phosphotriester linkages.

The nucleic acids used in the present invention will also include those nucleic acids in which modifications have been made in one or more sugar moieties and/or in one or more of the pyrimidine or purine bases. Examples of sugar modifications include replacement of one or more hydroxyl groups with halogens, alkyl groups, amines, azido groups or functionalized as ethers or esters. Additionally, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

Multiple genetic sequences can be also be used in the present methods. Thus, the sequences for different proteins may be located on one strand or plasmid. Promoter, enhancer, stress or chemically-regulated promoters, antibiotic-sensitive or nutrient-sensitive regions, as well as therapeutic protein encoding sequences, may be included as required. Non-encoding sequences may be also be present, to the extent that they are necessary to achieve appropriate expression.

The nucleic acids used in the present method can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available. See, for example, Itakara, U.S. Pat. No. 4,401,796; Caruthers, et al., U.S. Pat. Nos. 4,458,066 and 4,500,707; Beaucage, et al., *Tetrahedron Lett.,* 22:1859–1862 (1981); Matteucci, et al., *J. Am. Chem. Soc.,* 103:3185–3191 (1981); Caruthers, et al., *Genetic Engineering,* 4:1–17 (1982); Jones, chapter 2, Atkinson, et al., chapter 3, and Sproat, et al., chapter 4, in *Oligonucleotide Synthesis: A Practical Approach,* Gait (ed.), IRL Press, Washington D.C. (1984); Froehler, et al., *Tetrahedron Lett.,* 27:469–472 (1986); Froehler, et al., *Nucleic Acids Res.,* 14:5399–5407 (1986); Sinha, et al. *Tetrahedron Lett.,* 24:5843–5846 (1983); and Sinha, et al., *Nucl. Acids Res.,* 12:4539–4557 (1984) which are incorporated herein by reference.

Formation of the cationic liposome-nucleic acid complexes is carried out by first equilibrating the liposome solution and the nucleic acid solution to a temperature of about 0° C. to about 12° C., preferably about 2° C. to about 7° C., more preferably about 4° C. Combination of the two pre-cooled solutions provides a single mixture in which the complexes form. In preferred embodiments, the first solution of cationic liposomes and the second solution of nucleic acids are combined and incubated at temperatures of from about 0° C. to about 10° C. for a period of time of from about 10 to about 60 minutes. Mixing of the two solutions can be carried out using any gentle mixing processes which will not disrupt the liposomes and complexes formed therefrom. When complexes are formed on small-scale, the mixing will preferably be via pipet mixing. For a larger scale production of complexes, mixing can be carried out using a gentle vortex motion.

The cationic liposome/nucleic acid complexes formed by the above methods will typically have a mean diameter of from about 200 to about 350 nm, preferably about 250 to about 300 nm.

IV. Pharmaceutical Preparations

The cationic liposome/nucleic acid complexes prepared by the above methods can be administered either alone or in mixture with a physiologically-acceptable carrier (such as physiological saline or phosphate buffer) selected in accordance with the route of administration and standard pharmaceutical practice.

Pharmaceutical compositions comprising the cationic liposome/nucleic acid complexes of the invention are prepared according to standard techniques and further comprise a pharmaceutically acceptable carrier. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. In compositions comprising saline or other salt containing carriers, the carrier is preferably added following complex formation. Thus, after the complex is formed, the complex can be diluted into pharmaceutically acceptable carriers such as normal saline. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the complex suspension may include lipid-protective agents which protect lipids against free-radical and lipid-peroxidative damages on storage. Lipophilic free-radical quenchers, such as α-tocopherol and water-soluble iron-specific chelators, such as ferrioxamine, are suitable.

The concentration of complexes in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, complexes composed of irritating lipids may be diluted to low concentrations to lessen inflammation at the site of administration. In one group of embodiments, the nucleic acid will have an attached label and will be used for diagnosis (by indicating the presence of complementary nucleic acid). In this instance, the amount of complexes administered will depend upon the particular label used, the disease state being diagnosed and the judgement of the clinician but will generally be between about 0.01 and about 50 mg per kilogram of body weight, preferably between about 0.1 and about 5 mg/kg of body weight.

As noted above, it is often desirable to include polyethylene glycol (PEG)-modified phospholipids, PEG-ceramide, or ganglioside $G_{M1}$-modified lipids to the complexes. Addition of such components prevents complex aggregation and provides a means for increasing circulation lifetime and increasing the delivery of the lipid-nucleic acid complexes to the target tissues. Typically, the concentration of the PEG-modified phospholipids, PEG-ceramide or $G_{M1}$-modified lipids in the complex will be about 1–15%. In a particularly preferred embodiment, the PEG-modified lipid is a PEG-ceramide.

The present invention also provides cationic liposome/nucleic acid complexes in kit form. The kit will typically be comprised of a container which is compartmentalized for holding the various elements of the kit. The kit will contain the compositions of the present inventions, preferably in dehydrated form, with instructions for their rehydration and administration. In still other embodiments, the complexes and/or compositions comprising the complexes will have a targeting moiety attached to the surface of the complex. Methods of attaching targeting moieties (e.g., antibodies, proteins) to lipids (such as those used in the present complexes) are known to those of skill in the art.

Dosage for the cationic liposome/nucleic acid formulations will depend on the ratio of nucleic acid to lipid and the administrating physician's opinion based on age, weight, and condition of the patient.

V. Methods of Transfecting Cells

The cationic liposome/nucleic acid complexes of the present invention are useful for the introduction of nucleic acids, preferably plasmids into cells. Accordingly, the present invention also provides methods for introducing a nucleic acid or plasmid into a cell. The methods are carried out in vitro or in vivo by first forming the complexes as described above, then contacting the complexes with the cells for a period of time sufficient for transfection to occur.

The complexes of the present invention can be adsorbed to almost any cell type. Once adsorbed, the complexes can either be endocytosed by a portion of the cells, exchange lipids with cell membranes, or fuse with the cells. Transfer or incorporation of the nucleic acid portion of the complex can take place via any one of these pathways. In particular, when fusion takes place, the liposome or complex membrane is integrated into the cell membrane and the contents of the complex or liposome combine with the intracellular fluid. Contact between the cells and the cationic liposome/nucleic acid complexes, when carried out in vitro, will take place in a biologically compatible medium. The concentration of complexes can vary widely depending on the particular application, but is generally between about 1 μmol and about 10 mmol. Treatment of the cells with the cationic liposome/nucleic acid complexes will generally be carried out at physiological temperatures (about 37° C.) for periods of time of from about 1 to 6 hours, preferably of from about 2 to 4 hours. For in vitro applications, the delivery of nucleic acids can be to any cell grown in culture, whether of plant or animal origin, vertebrate or invertebrate, and of any tissue or type. In preferred embodiments, the cells will be animal cells, more preferably mammalian cells, and most preferably human cells.

In one group of preferred embodiments, a cationic liposome/nucleic acid suspension is added to 60–80% confluent plated cells having a cell density of from about $10^3$ to about $10^5$ cells/mL, more preferably about $2 \times 10^4$ cells/mL. The concentration of the suspension added to the cells is preferably of from about 0.01 to 0.2 μg/mL, more preferably about 0.1 μg/mL.

Typical applications include using well known transfection procedures to provide intracellular delivery of DNA or mRNA sequences which code for therapeutically useful polypeptides. In this manner, therapy is provided for genetic diseases by supplying deficient or absent gene products (i.e., for Duchenne's dystrophy, see Kunkel, et al., *Brit. Med. Bull.* 45(3):630–643 (1989), and for cystic fibrosis, see Goodfellow, *Nature* 341:102–103 (1989)). Other uses for the compositions of the present invention include introduction of antisense oligonucleotides in cells (see, Bennett, et al., *Mol. Pharm.* 41:1023–1033 (1992)).

Alternatively, the compositions of the present invention can also be used for the transfection of cells in vivo, using methods which are known to those of skill in the art. In particular, Zhu, et al., *Science* 261:209–211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250–256 (1993), incorporated herein by reference, describes the delivery of the cystic fibrosis transmembrane conductance regulator (CFTR) gene to epithelia of the airway and to alveoli in the lung of mice, using liposomes. Brigham, et al., *Am. J. Med. Sci.* 298:278–281 (1989), incorporated herein by reference, describes the in vivo transfection of lungs of mice with a functioning prokaryotic gene encoding the intracellular enzyme, chloramphenicol acetyltransferase (CAT).

For in vivo administration, the pharmaceutical compositions are preferably administered parenterally, i.e., intraarticularly, intravenously, intraperitoneally, subcutaneously, or intramuscularly. More preferably, the pharmaceutical compositions are administered intravenously or intraperitoneally by a bolus injection. For example, see Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York. 101:512–527 (1983); Mannino, et al., *Biotechniques* 6:682–690 (1988); Nicolau, et al., *Crit. Rev. Ther. Drug Carrier Syst.* 6:239–271 (1989), and Behr, *Acc. Chem. Res.* 26:274–278 (1993). Still other methods of administering lipid-based therapeutics are described in, for example, Rahman et al., U.S. Pat. No. 3,993,754; Sears, U.S. Pat. No. 4,145,410; Papahadjopoulos et al., U.S. Pat. No. 4,235,871; Schneider, U.S. Pat. No. 4,224,179; Lenk et al., U.S. Pat. No. 4,522,803; and Fountain et al., U.S. Pat. No. 4,588,578.

In other methods, the pharmaceutical preparations may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures which include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue. "Closed" procedures are invasive procedures in which the internal target tissues are not directly visualized, but accessed via inserting instruments through small wounds in the skin. For example, the preparations may be administered to the peritoneum by needle lavage. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

The cationic liposome/nucleic acid complexes can also be administered in an aerosol inhaled into the lungs (see, Brigham, et al., *Am. J. Sci.* 298(4):278–281 (1989)) or by direct injection at the site of disease (Culver, HUMAN GENE THERAPY, MaryAnn Liebert, Inc., Publishers, New York. pp.70–71 (1994)).

The methods of the present invention may be practiced in a variety of hosts. Preferred hosts include mammalian species, such as humans, non-human primates, dogs, cats, cattle, horses, sheep, and the like.

VI. EXAMPLES

Materials and Methods:

DODAC (dioleoyldimethylammonium chloride) was synthesized and supplied by Steven Ansell of Inex Pharmaceuticals Inc. (Vancouver, B.C.) according to methods outlined in co-pending application Ser. No. 08/536,584 (Attorney Docket No. 16303-001820), the disclosure of which is incorporated herein by reference. DOPE (dioleoylphosphatidylethanolamine) was purchased from Avanti Polar Lipids (Alabaster, Ala.). $^{14}$C-CHE (cholesterylhexadecyl ether) and $^{14}$C-DOPE were obtained from Amersham (Oakville, Ont.). Chloramphenicol acetyltransferase (CAT) and lactose was obtained from Sigma (St. Louis, Mo.). All other chemicals used in this study were reagent grade.

The plasmid pInex CAT v2.0, containing the *Escherichia coli* CAT gene under the control of the CMV promoter was constructed and provided by Roger Graham of Inex Pharmaceuticals Inc. (Vancouver, B.C.). Briefly, the CAT gene, containing the alfalfa mosaic virus (AMV) translational enhancer, was cleaved from pCMV4CAT plasmid (generously provided by K. Brigham, Toronto) using Not I restriction endonuclease. Similarly the Not I fragment of pCMV (obtained from Clontech (Palo Alto, Calif.) was removed, and the CAT gene inserted into this site. The resulting plasmid, pInex CAT v2.0 is 4490 bp and includes the CMV promoter, the SV40 intron for processing the message, the AMV enhancer and the SV40 polyadenylation signals. The plasmid was isolated by standard molecular techniques (Sambrook et al., 1989) and purified using a Qiagen Plasmid Purification Kit (Qiagen, Chatsworth, Calif.). The nucleic acid concentration was measured by UV absorption at 260 nm and verified by electrophoresis on 0.8% agarose gels.

Radiolabeled plasmid was generated by culturing *Escherichia coli* pInex CAT v2.0 with $^{3}$H-thymidine-5'-triphosphate (Dupont/NEN, Boston, Mass.) and purified using standard techniques as described above. Specific activity of $^{3}$H-pInex CAT v2.0 was approximately 200,000 dpm/µg.

The murine B16/BL6 melanoma cell line was obtained from National Cancer Institute Tumour Repository 12-105-54 (Bethesda, Md.) and was maintained in Eagles Minimal Essential Medium supplemented with 5% FBS at 37° C. in 5% $CO_2$ with no antibiotics. Cells used in this study were subcultured about 20 times.

Example 1

This example illustrates the preparation of the cationic liposomes/nucleic acid complexes of the present invention.

DODAC:DOPE liposomes (50:50 mol %) were prepared according the method of Hope et al, *Biochem. Biophys. Acta* 812:55–65 (1985). Lipids were dissolved in chloroform (20 mg/mL), radiolabeled at a specific activity of 1–2 µCi/50 mg with $^{14}$C-CHE as a non-metabolizable and non-exchangeable liposomal marker (Scherphof et al., *Biochem. Soc. Trans.* 15:625–628 (1987)). For tracking radiolabeled lipid following injection, $^{14}$C-DOPE was used as the liposomal marker. The lipids were dried to a thin film under a stream of nitrogen gas and vacuum dried at >76 cm Hg for at least 4 hours. The films were hydrated in filter sterilized 300 mM lactose and passed 10 times at room temperature through an extruder (Lipex Biomembranes, Vancouver, B.C.) containing 3 stacked 80 nm polycarbonate membranes. The lipid concentration of the resulting liposome vesicles was calculated by multiplying the ratio of dpms from $^{14}$C-CHE or $^{14}$C-DOPE (Packard TR 1900 Scintillation Counter) before and after extrusion by the initial known lipid concentration. The size of the liposomes was measured by QELS using a Nicomp Submicron Particle Sizer (Model 270, Pacific Scientific, Santa Barbara, Calif.) operating at a wavelength of 632.8 nm. All liposomes had a mean diameter of 100 to 140 nm by Gaussian analysis and were stored at 4° C. until use.

Prior to use, liposomes were diluted in sterile 300 mM lactose on ice to a final lipid concentration ranging from 1000 to 4000 nmoles/mL. DNA (pInex CAT v2.0) was diluted in sterile 300 mM lactose on ice at concentrations ranging from 100 to 400 µg/mL. An equal volume of DNA was added to liposomes with mixing. DNA/liposome complexes were incubated on ice for 30 minutes prior to use.

Example 2

This example provides an evaluation of transfection using conjugates prepared according to Example 1.

Adult female C57BL/6J mice (7 to 8 weeks old) were used for all experiments. All procedures were performed in accordance with Canadian Council of Animal Care guidelines for the care and use of laboratory animals. Mice ($\geq 4$ per group) were injected with B16/BL6 murine tumour cells i.p. ($1 \times 10^5$ cells) in Hanks' balanced salt solution (HBSS) in a volume of 0.5 mL. The tumours were allowed to grow for 7, 10 or 13 days. The mice were injected i.p. with complexes at the appropriate liposome and DNA concentration. After 24, 48 or 72 hr, the tumours were harvested, weighed and stored at $-70°$ C. until assayed for chloramphenicol acetyltransferase (CAT) activity.

2.1 Assay of CAT Activity:

Tumours were excised, weighed and stored at $-70°$ C. for <one week prior to processing. Tumours were thawed in the presence of buffer (15 mM TRIS-HCl pH=8.0, 60 mM KCl, 15 mM NaCl, 5 mM EDTA pH=8.0, 0.15 mM spermine, 1.0 mM DTT, 35 $\mu$g/mL PMSF, 0.5 $\mu$g/mL leupeptin, 0.5 $\mu$g/mL aprotinin, 5 $\mu$M paraoxon) to make a final concentration of 10% (w/v). Tumours were homogenized on ice using a Polytron homogenizer (Brinkman Instruments Canada, Mississauga, ON). Samples 100 $\mu$l were transferred to 1.5 mL microfuge tubes and subjected to three cycles of freeze/thaw consisting of immersion in liquid nitrogen followed by thawing in a 37° C. water bath. Samples were centrifuged at 10,000 rpm in an Eppendorf microcentrifuge for 10 min at room temperature; the supernatants were recovered and heat inactivated for 15 min at 65° C. Samples were centrifuged for 10 min at 10,000 rpm and 55 $\mu$l of the supernatant from each sample was evaluated for CAT activity. To each sample, 50 $\mu$l (250,000 dpm) of $^{14}$C-chloramphenicol (NEN-Dupont, Boston, Mass.) and 25 $\mu$l N-butyryl Co-A (5 mg/mL) was added and incubated at 37° C. for 2 h. Mixed xylenes (Aldrich Chemical Co., Milwaukee, Wis.) (300 $\mu$l) were added to each tube and vortexed vigorously for 30 sec, followed by centrifugation for 3 min at 10,000 rpm in an eppendorf microcentrifuge at room temperature. The upper phase was transferred to a fresh microfuge tube and 750 $\mu$l buffer (15 mM TRIS-HCl, pH=8.0, 60 mM KCl, 15 mM NaCl, 5 mM EDTA; pH 8.0) was added to each sample, vortexed and recentrifuged. For each sample, 100 $\mu$L of the resulting upper phase was sampled, 5 mL Picofluor scintillant (Packard Instrument Co., Meriden, Conn.) was added and radioactivity ($^{14}$C) determined in a Canberra-Packard scintillation counter (1900 TR Tri Carb). CAT units were determined by comparison to a standard curve generated for each experiment. Values were converted to and expressed as mU CAT/g wet weight. Each CAT assay was performed in triplicate and expressed +/-S.E.

2.2 Quantification of Plasmid DNA Following Transfection:

Mice bearing 7 day B16/BL6 i.p. tumours were transfected with DODAC/DOPE liposome/pInex Cat v2.0 complexes or free plasmid as described. Two hr and 24 hr following transfection, mice were killed and lavaged with three mL HBSS. Blood was obtained by cardiac puncture and the lavage and blood were immediately analyzed for the presence of plasmid DNA. Tumour, spleen, pancreas and liver were excised, weighed and stored at $-20°$ C. until further analyzed. Plasmid DNA associated with tumour tissue was quantified by two methods. First, tumours (and spleen, liver, pancreas, blood and lavage) were evaluated for the presence of $^3$H following transfection with $^3$H-pInex Cat v2.0. Briefly, blood (100 $\mu$l), lavage (1 mL), whole tumour, spleen and pancreas were incubated with 0.5 mL Solvable (NEN/Dupont) at 50° C. for 18 hr. Liver was homogenized in water to make a 25% homogenate and 200 $\mu$L was added to 0.5 mL Solvable and incubated as described. The samples were subsequently decolourized by the addition of $H_2O_2$ and HCl, scintillation fluid added and the samples counted for $^{14}$C radioactivity. The second method involved evaluating the tumours for the presence of plasmid DNA using dot blot analysis. Freshly collected tumour tissue was homogenized for 20 sec on ice using Polytron homogenizer in buffer used for CAT assay (100 mg tumour per mL buffer). One hundred $\mu$l homogenate was removed from each sample and dissolved in DNAzol (Gibco/BRL, NY) at room temperature for 30 min. Cold 95% ethanol was added to each tube (1 mL) and the DNA precipitated for 1 hr at room temperature. DNA pellets were recovered by centrifugation at 10,000 rpm for 10 min at room temperature, rinsed with 70% ethanol and dissolved in 100 $\mu$l TE (10 mM TRIS-HCl, pH=8.0, 1 mM EDTA, pH=8.0). Purified DNA was applied to nitrocellulose membrane using a dot blot apparatus and the blots were hybridized using $^{32}$P random prime-labeled pInex CAT v2.0 as described by Sambrook et al (1989). Plasmid DNA associated with tumours 2 and 24 hr following transfection was quantified using a PhosphoImager (Molecular Dynamics, Sunnyvale, Calif.). pInex CAT v2.0-specific DNA values were standardized using known pInex CAT v2.0 standards. Four animals were evaluated for the 2 and 24 hr time points with three replications per assay. Data are expressed as means +/-S.E.

2.3 Assessment of Intact DNA:

Plasmid DNA associated with tumours 2 hr and 24 hr following transfection with liposome/DNA complexes was isolated along with genomic DNA using standard SDS/proteinase K techniques (Sambrook et al., 1989). DNA was extracted by phenol/chloroform and precipitated with 2.5 vol 95% ethanol. The DNA was resuspended in TE buffer (10 mM Tris-HCl pH=8.0, 1 mM EDTA) and evaluated for concentration using densitometric readings at $A_{260}$. DNA samples were loaded onto a 1% agarose gel and subjected to electrophoresis at 5V in TBE buffer (89 mM TRIS-Borate, 2 mM EDTA) for 18 hr. The DNA was transferred to nitrocellulose membrane and hybridized with $^{32}$P random prime-labeled pInex CAT v2.0 following Sambrook et al (1989). The hybridized blot was exposed and the image digitized using a PhosphoImager (Molecular Dynamics, Calif.).

2.4 Statistical Analysis:

Quantitative data generated for CAT activity were statically evaluated using analysis of variance test from Statistica (Statistical Software Inc., Tulsa, Okla.).

Figure 2:
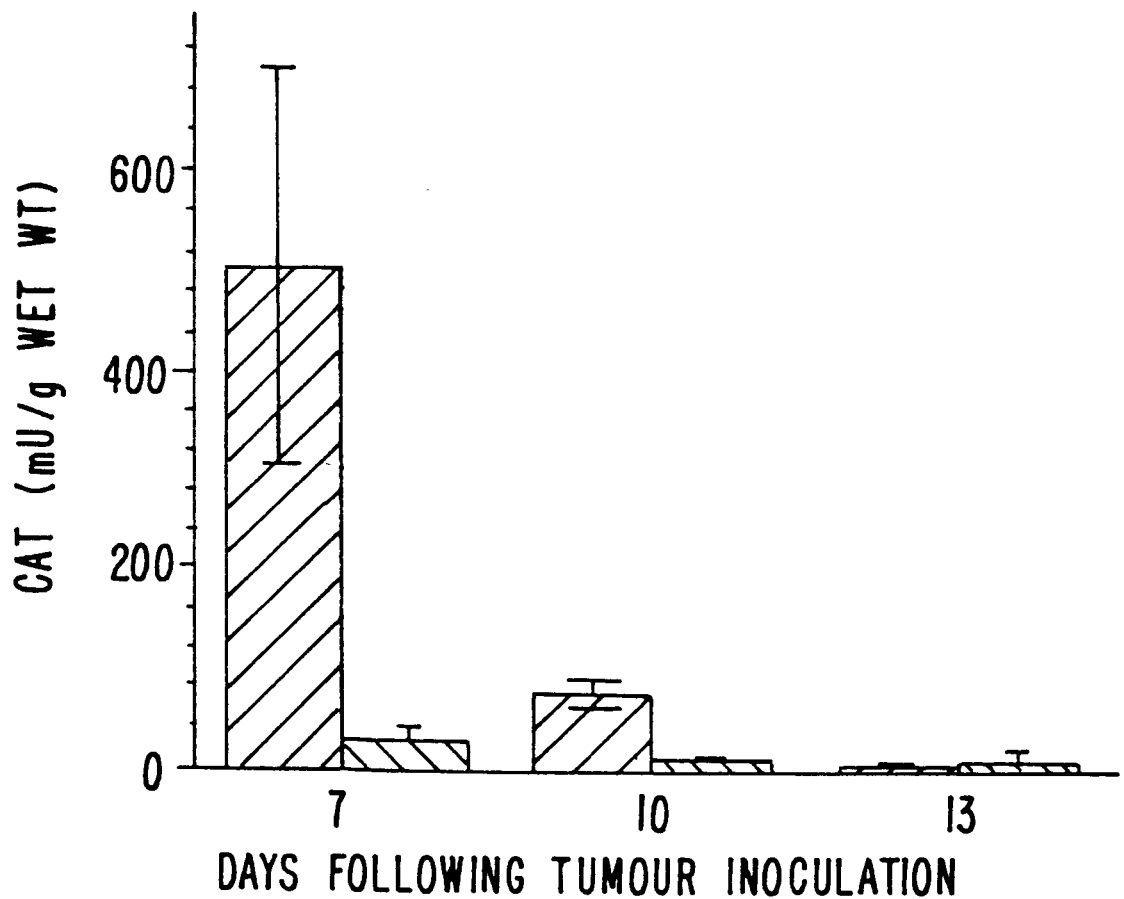
FIG. 2 illustrates the CAT activity expressed 24 hr following transfection of B16/BL6 melanoma tumours grown i.p. for 7, 10 or 13 days with DODAC/DOPE/pInex CAT v2.0 (light gray) or free pInex CAT v2.0 DNA (dark gray). Animals were administered 25 μg plasmid DNA in a volume of 500 μL 300 mM lactose. Ratio of lipid to DNA was 10 nmoles/μg DNA. The levels of CAT activity were determined based on known standards and expressed as mU/g wet weight. Each bar represents the mean ±S.E. of n≧4.

2.5 CAT expression in melanoma tumours:

C57BL/6J mice were injected i.p. with B16/BL6 melanoma cells and tumours allowed to grow for 7, 10 or 13 days. Cationic liposome/DNA complexes were prepared in sterile 300 mM lactose using DODAC/DOPE (50:50 mol %) and pInex CAT v2.0 plasmid at a ratio of 10:1 (nmoles lipid: $\mu$g DNA). Twenty five $\mu$g of DODAC/DOPE liposome/DNA complexes were injected i.p. in a volume of 500 $\mu$l. Two days following transfection, the tumours were excised and the level of gene expression was determined by measuring CAT activity (FIG. 2). Tumours grown for 7, 10 or 13 days and treated with free plasmid DNA had levels of CAT activity ranging from 13.2 mU/g wet weight to 30.4 mU/g wet weight. In contrast, tumours that were grown for 7 days and treated with DODAC/DOPE liposome/DNA complexes had higher levels of CAT activity (approximately 500 mU/g wet weight). This level of expression decreased when the tumours progressed for longer times (10 and 13 days). B16/BL6 tumours grown i.p. in C57BL/6J mice for 7 days were used for the remainder of this study.

Figure 3:
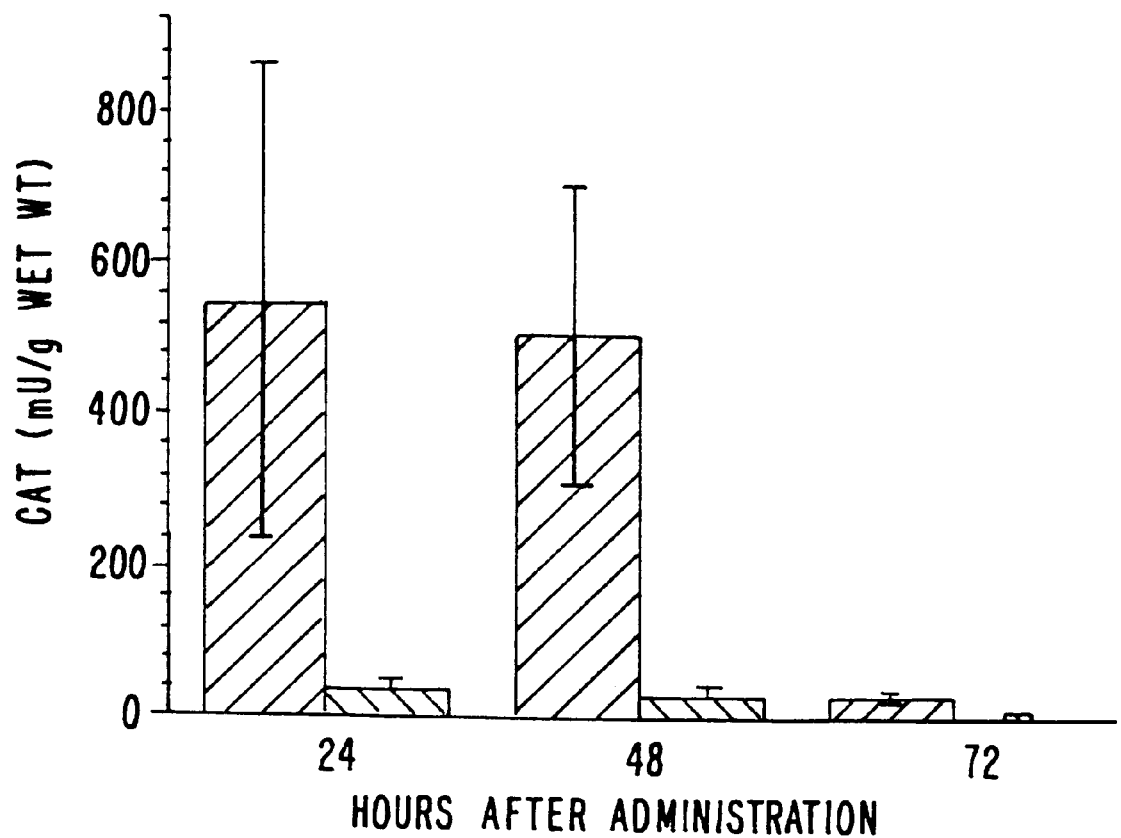
FIG. 3 illustrates the CAT activity expressed in B16/BL6 i.p tumours grown for 7 days and evaluated 24, 48 or 72 hr following i.p. transfection with DODAC/DOPE/pInex CAT v2.0 (light gray) or free pInex CAT v2.0 DNA (dark gray). Animals were administered 25 μg plasmid DNA in a volume of 500 μL 300 mM lactose. Ratio of lipid to DNA was 10 nmoles/μg DNA. The levels of CAT activity were determined based on known standards and expressed as mU/g wet weight. Each bar represents the mean ±S.E. of n≧3.

To determine the time course of CAT expression, tumours were grown for 7 days and excised 24, 48 or 72 hr following injection of free DNA or liposome/DNA complexes. CAT activity was determined and the results are shown in FIG. 3. CAT expression from tumours excised from animals treated with liposome/DNA complexes was approximately 500 mU/g wet weight if assayed 24 and 48 hr after i.p. administration. This was shown to be substantially higher than expression obtained following administration of free DNA alone (30.43 to 38.71 mU/g wet weight). By 72 hr after injection of liposome/DNA complexes, a decrease in CAT expression was observed (approximately 30 mU/g wet weight).

Figure 4:
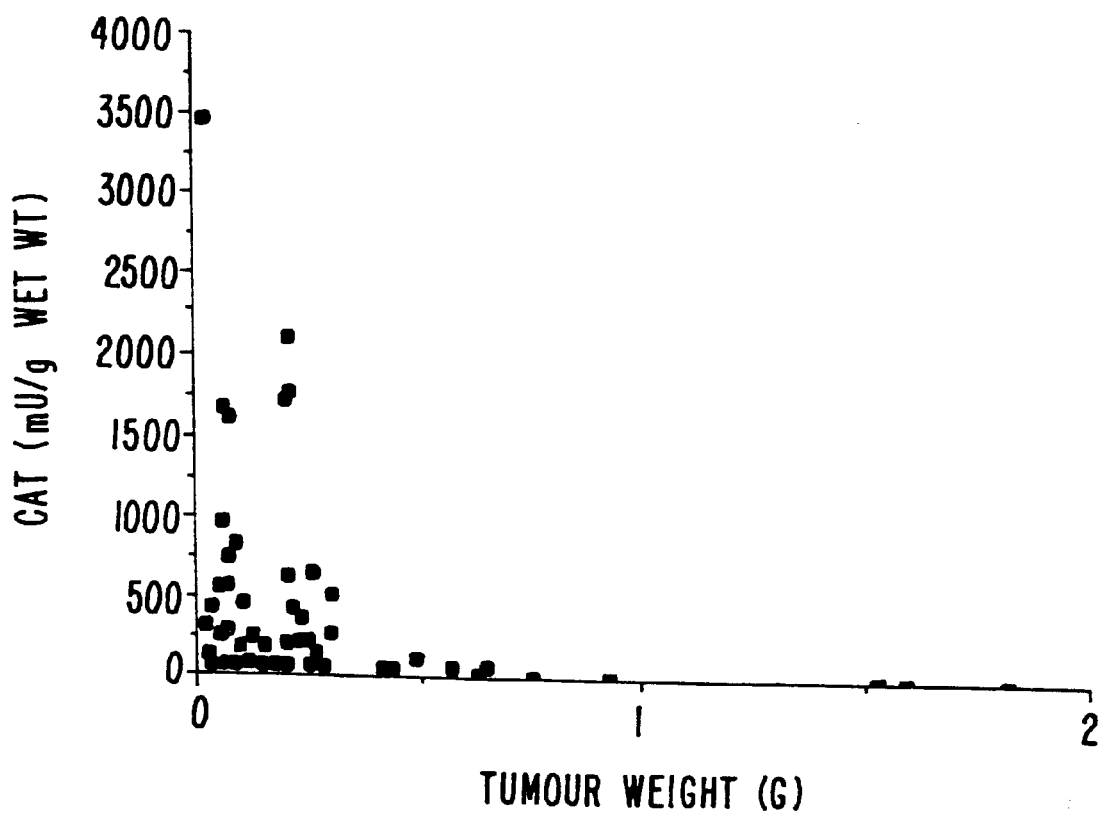
FIG. 4 illustrates the effect of tumour weight on CAT activity. Data is included from all experiments completed with liposome/DNA complexes and CAT activity was expressed in mU/g wet weight as a function of tumour weight.

The results presented in FIGS. 2 and 3 indicate that transfection activity decreases as tumour size increases. For this reason, expression was evaluated as a function of tumour size. FIG. 4 shows a graph of tumour weights and their corresponding CAT activity for all experiments completed using liposome/DNA complexes. These data clearly shows that CAT activity in small tumours (<100 mg) is higher than CAT activity in larger tumours (>200 mg). It appears that the size of the tumour, therefore, is important in evaluating in vivo transfection efficiency following i.p. injection of these cationic liposome/DNA complexes, a parameter that may be a function of accessibility of the DNA to the tumour cells.

Figure 5:
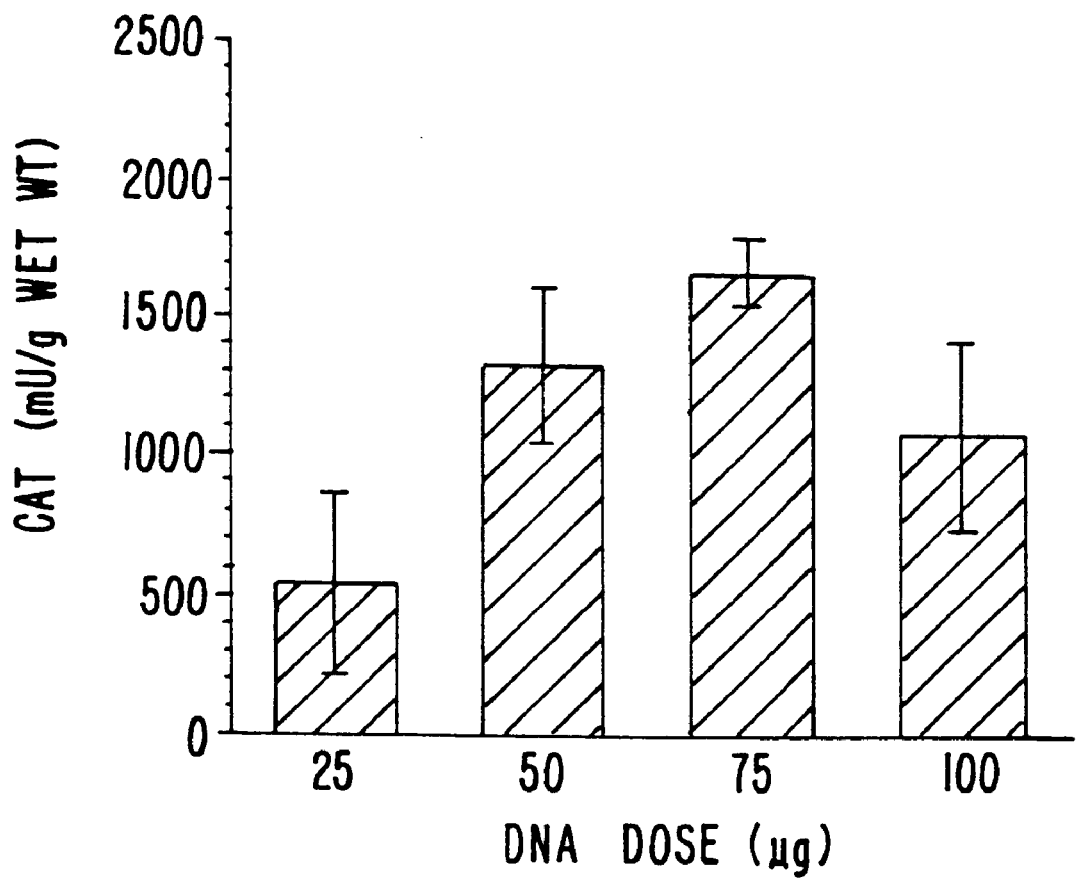
FIG. 5 illustrates the effect of DNA dosage on CAT activity following transfection of B16/BL6 i.p. tumours with DODAC/DOPE/pInex CAT v2.0. Animals were injected with various amount of lipid and DNA (ratio 10 nmoles lipid/μg DNA) in 500 μL 300 mM lactose. The level of CAT activity was determined as in FIG. 1. Each bar represents mean ±S.E. (n≧3).

2.6 DNA Dose Response:

Having established that maximal CAT expression was obtained 24 hr following administration of complexes and that efficient transfection can be achieved when tumours are small, we evaluated whether higher transfection efficiencies could be achieved by modifying the dose of DNA administered. Increasing amounts of DNA were injected i.p. into animals bearing 7 day tumours; the tumours were harvested 24 hr later and evaluated for CAT activity (FIG. 5). In this experiment 25, 50, 75 and 100 μg of DNA were complexed with DODAC/DOPE liposomes such that the lipid:DNA ratio remained at 10 nmoles lipid:1 μg DNA. When 50 μg and 75 μg plasmid DNA were administered, CAT activities of 1334±286 and 1674±124 mU/g wet weight were obtained, respectively. These CAT activities were higher than those obtained using 25 μg plasmid DNA (545±315 mU/g wet weight). Increasing the amount of DNA in the complexes to 100 μg yielded CAT activities of 1082±335 mU/g wet weight. Injection of free plasmid alone yielded CAT expression levels ranging from 39±11 mU/g wet weight for 25 μg DNA to 72±9 mU/g wet weight for 75 μg DNA (data not shown). These data indicate that there is an apparent increase in CAT activity as the DNA dose is increased, however, these differences are insignificant.

Figure 6:
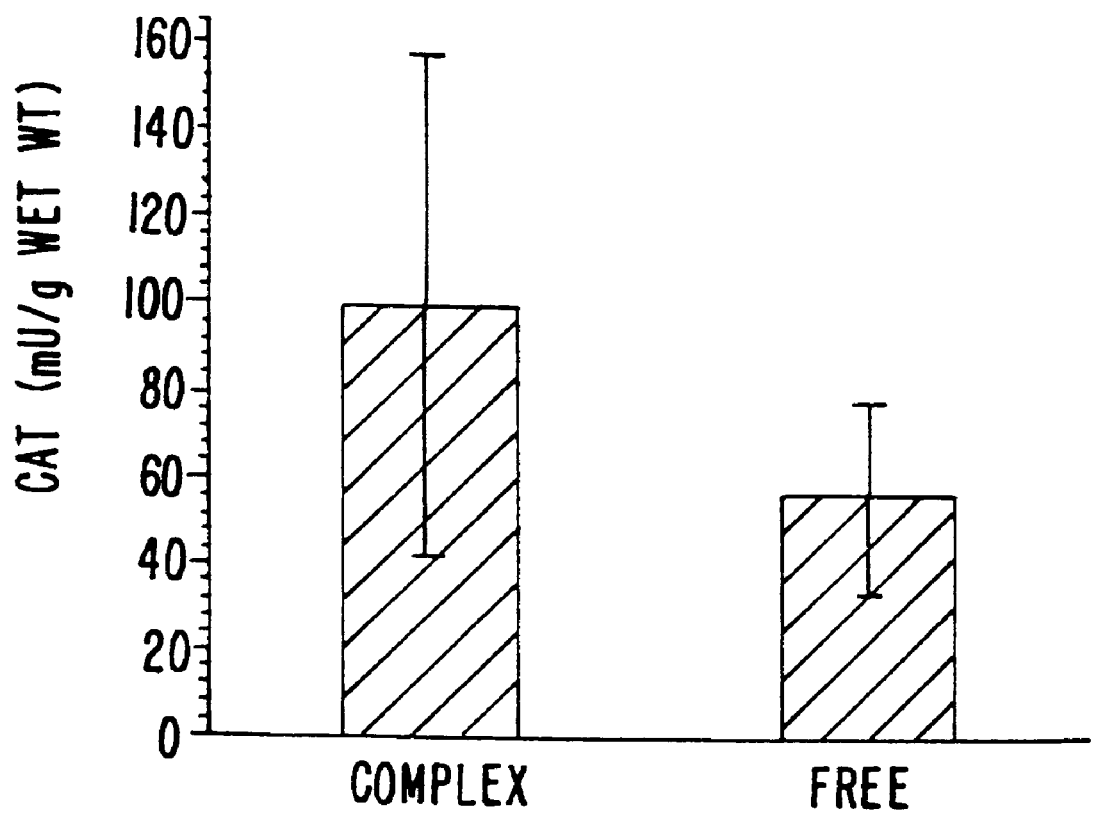
FIG. 6 illustrates the CAT activity expressed in 7 day B16/BL6 i.p. tumours following repetitive dosing of animals i.p. with DODAC/DOPE/pInex CAT v2.0 (complex) and free DNA (free). Animals were administered complexes or free DNA for three consecutive days and were given a DNA dose of 25 μg in a volume of 500 μL. CAT activity was expressed as mU/g wet weight and each bar represents the mean ±S.E. (n=7).

To determine if repeated dosing could increase transfection efficiency, 25 μg plasmid DNA complexed to DODAC/DOPE liposomes was injected into tumour bearing animals for 3 consecutive days. Twenty-four hr after the last injection (day 10), the tumours were harvested and assayed for CAT activity (FIG. 6). Free plasmid (25 μg) was also injected i.p. on three consecutive days for comparison. CAT activity in tumours from animals treated with multiple doses of free plasmid were not significantly different (p>0.99) from results obtained from a single injection (FIG. 3). CAT activity in tumours from animals administered 25 μg complexed plasmid DNA i.p. for three consecutive days was 100±57 mU/g wet weight. This was not different from the CAT activity in tumours from animals which were given 25 μg free plasmid DNA (56±21 mU/g wet weight). It is important to point out that the CAT activity observed following this repetitive dosing schedule with liposome/DNA complexes and yielded levels which were comparable to those observed in 10 day tumours (FIG. 2), consistent with the fact that CAT activities decreased as the tumour size increased. These data indicate that multiple injections of cationic liposome/DNA complexes does not enhance transfection efficiency in this system.

2.7 Plasmid DNA and Liposomal Lipid Biodistribution Following i.p. Administration:

Having established optimal conditions for transfection as described above, further experiments were carried out to evaluate the in vivo distribution of plasmid DNA and associated lipid following i.p. administration in tumour bearing animals. $^3$H-plasmid DNA was used to measure DNA delivery and $^{14}$C-DOPE as a liposomal lipid marker for the DODAC/DOPE liposomes. The distribution of $^3$H and $^{14}$C was evaluated in lavage, blood and tumours 30, 60 and 120 min following i.p. administration of DODAC/DOPE/pInex CAT v2.0 complexes. Free $^3$H-plasmid DNA and free $^{14}$C-DODAC/DOPE liposomes were also administered and used for comparison. The data from this experiment are presented in Table 1. There appeared to be no difference in the amount of $^3$H-plasmid DNA detected in the blood up to 120 min following i.p. administration whether the plasmid was given in free form (0.7±0.1 to 0.9±0.1 μg/mL) or complexed to DODAC/DOPE cationic liposomes (0.3±0.1 to 0.7±0.1 μg/mL). $^{14}$C-DOPE levels in the blood were evaluated, however, the values were below detection limits.

TABLE 1

Amount of $^3$H-plasmid DNA and $^{14}$C-lipid associated with lavage fluid, blood and tumours at various time points following i.p. administration of free DNA, free liposomes and DNA/liposome complexes. Results are expressed per ml blood, per g tumour tissue and total lavage (3 ml) as mean +/- S.E. for n = 5.

| Time | Free DNA (μg) | Free Liposomes (mmoles) | DNA/Liposome Complex DNA (μg) | (lipid (nmoles) |
|---|---|---|---|---|
| Blood | | | | |
| 30 | 0.7 ± 0.1 | ND | 0.3 ± 0.1 | ND |
| 60 | 0.9 ± 0.1 | ND | 0.6 ± 0.1 | ND |
| 120 | 0.9 ± 0.1 | ND | 0.7 ± 0.1 | ND |
| Lavage | | | | |
| 30 | 7.60 ± 2.04 | 34.04 ± 14.86 | 2.50 ± 0.23 | 46.54 ± 5.72 |
| 60 | 6.70 ± 2.03 | 50.32 ± 5.33 | 3.43 ± 0.54 | 53.32 ± 8.72 |
| 120 | 5.41 ± 1.16 | 41.80 ± 9.33 | 3.98 ± 0.42 | 55.60 ± 7.76 |
| Tumour | | | | |
| 30 | 4.74 ± 0.096 | 140.61 ± 57.98 | 21.21 ± 3.34 | 279.80 ± 46.01 |
| 60 | 6.60 ± 1.12 | 270.89 ± 45.95 | 22.14 ± 2.34 | 270.81 ± 33.11 |
| 120 | 7.85 ± 1.03 | 285.76 ± 45.96 | 46.01 ± 6.57 | 497.50 ± 60.11 |

Table 1 also shows the amount of DNA and lipid recovered in the lavage fluid after i.p. administration of free liposomes, free DNA or liposome/DNA complexes.

Approximately 20% of $^{14}$C-DOPE (up to 50.32±5.33 nmoles lipid) could be recovered in the lavage fluid at 30, 60 and 120 min after administration of liposomes alone and this level of lavage-associated lipid did not decrease over the time course. Approximately 30% of the injected dose of free DNA (up to 7.60±2.04 μg) was found in the lavage fluid following i.p. administration. When animals were given liposome/DNA complexes, the level of $^3$H-plasmid in the lavage fluid decreased while the level of $^{14}$C-DOPE remained similar to those obtained following administration of free DNA or control liposomes, respectively. From these data, >85% of the DNA administered as liposome/DNA complexes was no longer recoverable in the blood or lavage fluid even when the samples were collected 30 min after i.p. administration. It should be noted that the concentrations of liposomal lipid and DNA in the lavage fluid included peritoneal cell-associated as well as cell-free material.

B16/BL6 tumours in the peritoneal cavity of animals given liposome/DNA complexes were also assayed to determine the amount of $^3$H-plasmid DNA and $^{14}$C-lipid which was associated with this target tissue. Table 1 shows the amount of DNA and lipid associated per g tumour tissue. Analysis of $^3$H-plasmid DNA administered to animals in free form showed that there was an increase of approximately 2.0 fold in the amount of DNA associated with the tumours over the 120 min time course. Two hours after administration, 7.85±1.03 μg of DNA was isolated with the tumour. A similar increase in tumour-associated lipid was observed over the 2 hr time course after administration of free liposomes. When DNA/liposomes complexes were administered, the level of DNA associated with tumours increased significantly (4 to 6 fold) from animals administered with free DNA. The amount of DNA associated with tumours 120 min following administration of the liposome/DNA complexes was 46.01±6.57 μg and this corresponds to approximately 18% of the injected dose of $^3$H-DNA. A similar increase in tumour-associated lipid was observed compared to administration of free liposomes where approximately 500 nmoles lipid was associated with the tumours 120 min following administration of liposome/DNA complexes. This corresponds to approximately 20% of the injected dose of $^{14}$C-lipid. These results are remarkable considering the tumour size in these experiments was 100 mg or less.

Figure 7:
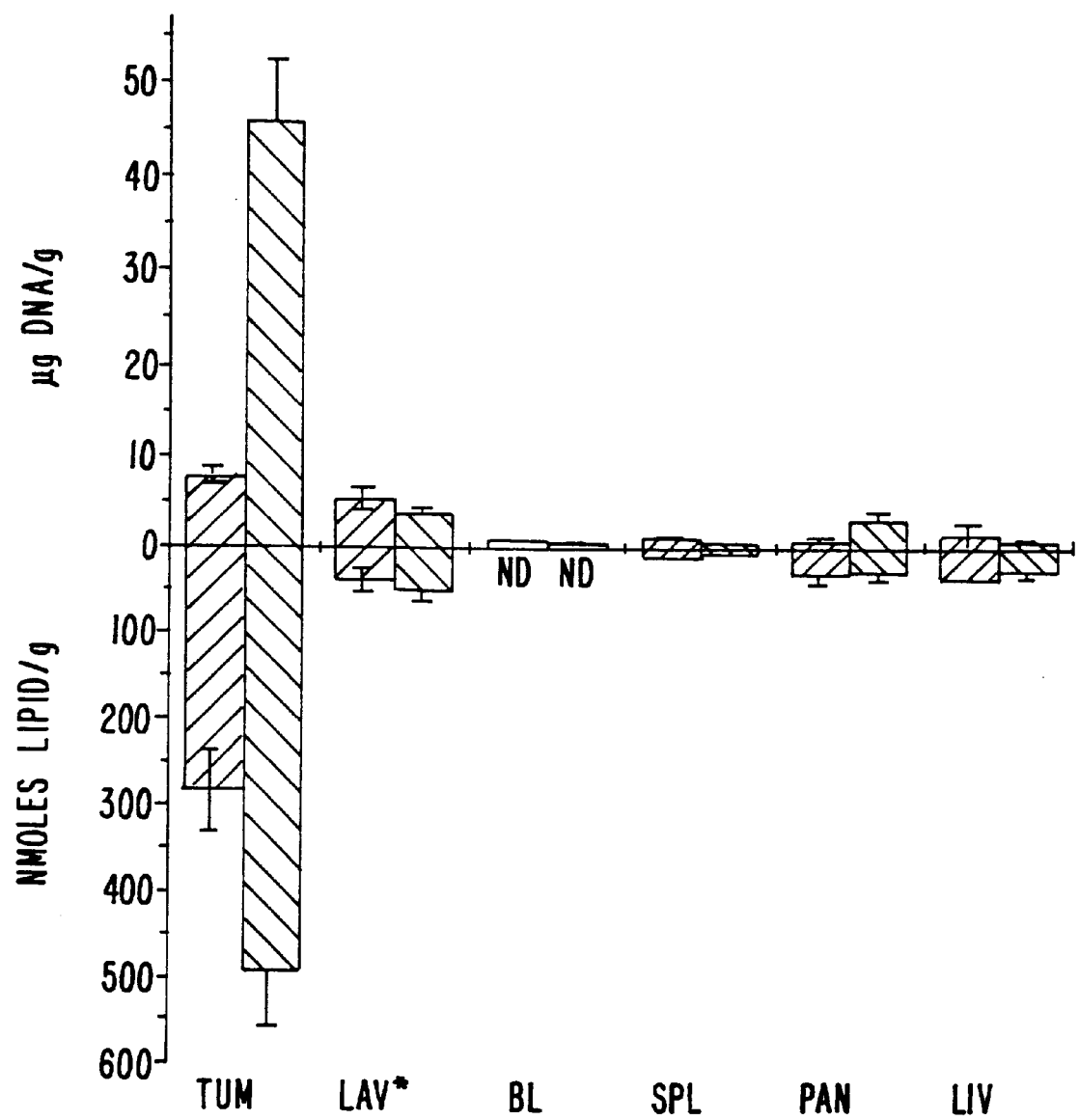
FIG. 7 illustrates the quantification of DNA (μg) and lipid (nmoles) 2 hr following i.p. administration of B16/BL6 i.p. tumours with DODAC/DOPE/pInex CAT v2.0 (dark gray) and free DNA (light gray) or free liposomes (light gray) in different tissues. DNA and lipid associated with tumour (tum), spleen (spl), pancreas (pan), liver (liv) and blood (bl) were expressed per g tissue ( S.E. (n=4 to 8). *DNA and lipid associated with lavage fluid (lav) was expressed per total lavage (3 mL). ND=not detected.

To determine whether this unexpectedly high level of tumour-associated lipid and DNA was specific to tumour tissue, we evaluated other (colateral) tissues for the presence of $^3$H-DNA and $^{14}$C-lipid. The data for these experiments are shown in FIG. 7 and includes the amount of DNA and lipid ($^{14}$C-DOPE) associated with tumour, lavage fluid, blood, spleen, pancreas and liver 120 min following i.p. administration. The light bars represent free DNA (top) or free liposomes (bottom) while the dark bars represent DNA (top) and lipid (bottom) following administration of liposome/DNA complexes. The amount of DNA and lipid measured in other tissues was significantly lower than that measured in tumours when evaluated on a per g basis. Less than 5% of the injected dose was found to be associated with these tissues when animals were administered free DNA, free liposomes or liposome/DNA complexes with the exception of liver where accumulations of up to 18% of the injected dose of $^{14}$C-DOPE were, observed. It should be noted that only a small amount of DNA (<3.0% of injected dose) and no liposomal lipid was detectable in 1 mL blood when the animals were given i.p. injection of either free DNA, free liposomes or liposome/DNA complexes. These data are consistent with the previous results and indicate that a substantial amount of DNA and lipid is specifically associated with the tumours following i.p. injection of DODAC/DOPE complexed plasmid DNA. This remarkable and high level of lipid and DNA association may be a simple consequence of the fact that free liposomes appear to be associated directly with the tumour after i.p. administration. It should be emphasized, however, that there are significant morphological changes in the liposomes following addition of plasmid DNA and it is known that these changes result in different chemical attributes in general and surface charge in particular. Both liposomes and liposome/DNA complexes are thought to exhibit a positive charge.

Figure 8:
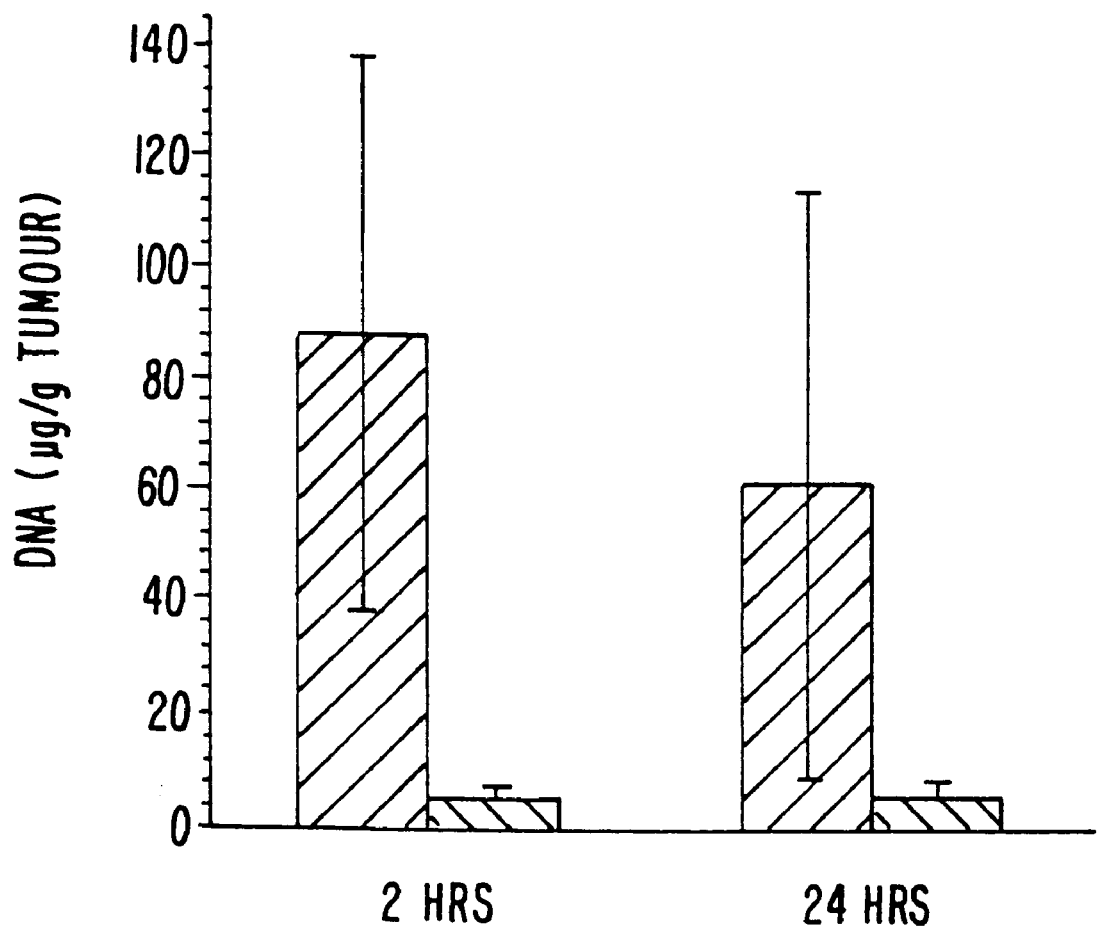
FIG. 8 illustrates the quantification of DNA by dot blot analysis associated with 7 day B16/BL6 i.p. tumours 2 hr and 24 hr following administration of DODAC/DOPE/pInex CAT v2.0 (light gray) and free DNA (dark gray). Each bar represents mean ±S.E. (n≧3).

As such a large amount of DNA was not expected to specifically associate with tumours, the amount of DNA was further quantified using dot blot analysis, an assay that specifically detects the presence plasmid DNA sequences. Tumour bearing animals were treated with free DNA and liposome/DNA complexes as described. Tumours were isolated 2 hr and 24 hr following transfection. Genomic and plasmid DNA was then isolated and blotted onto nitrocellulose membranes. DNA was quantified from dot blots using $^{32}$P random prime-labeled plasmid hybridization and the results analyzed using a phosphoimager (FIG. 8). The amount of DNA associated with tumours per g at 2 hr and 24 hr following transfection of free DNA was 5.86±1.42 μg and 6.33±2.26 μg respectively. The values obtained at 2 hr are consistent with results observed using $^3$H-plasmid DNA analysis (7.85±1.03 μg). The amount of DNA associated with the tumours 2 hr and 24 hr following transfection of liposome/DNA complexes was 88.72±50.58 and 61.29±53.10 μg respectively. Similar to free DNA, the amount of DNA associated with tumours 2 hr following administration of complexes does not appear to be different than that observed at 24 hr. Although the variability in this analysis is substantial the mean results are consistent with data obtained using $^3$H-plasmid DNA where analysis was performed 2 hr following administration of complexes. These data substantiate the fact that a surprisingly large amount of DNA (and lipid) is associated with B16/BL6 tumours following transfection with liposome/DNA complexes under the conditions employed. Furthermore, this large of amount of DNA remains associated with the tumours up to 24 hr following administration.

Figure 9:
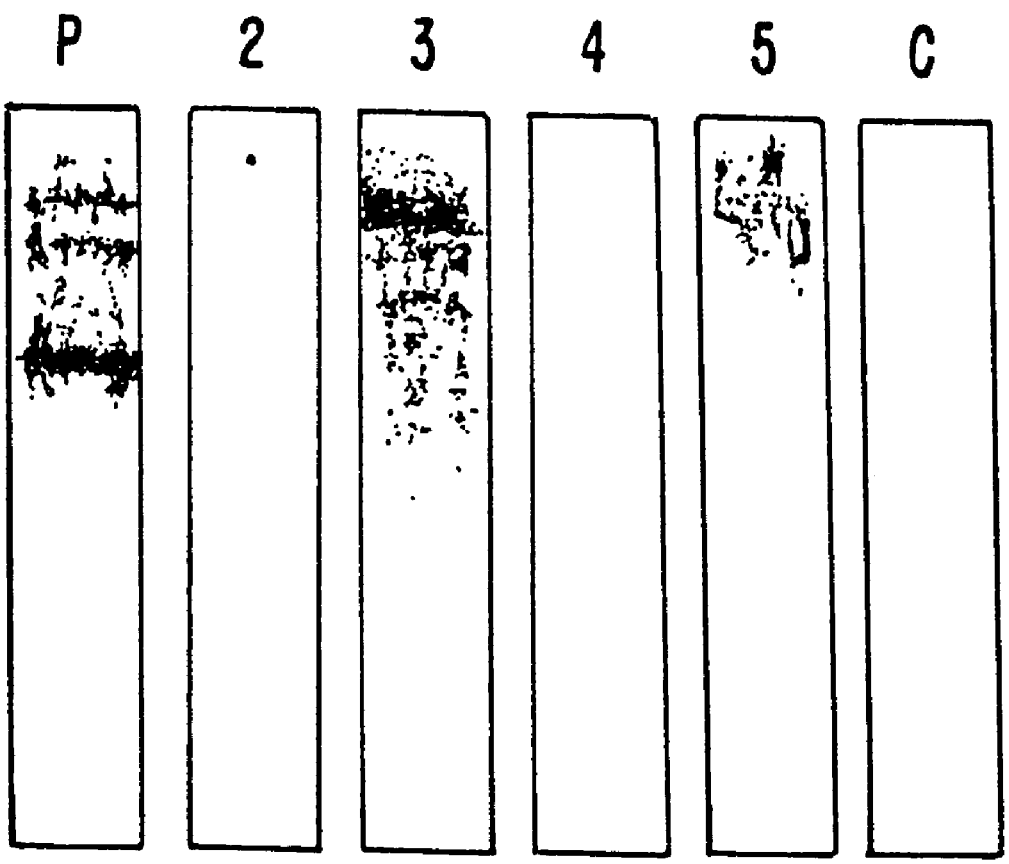
FIG. 9 shows a Southern blot of representative plasmid DNA from tumours following i.p. administration of DODAC/DOPE/pInex CAT v2.0 and free DNA to animals with 7 day B16/BL6 tumours. DNA was extracted from tumours and evaluated by Southern analysis 2 hr (lanes 2 and 3) and 24 hr (lanes 4 and 5) following transfection. M=molecular weight marker and C=control plasmid DNA.

2.8 DNA Integrity:

To determine whether plasmid DNA associated with tumours was intact, DNA integrity was evaluated by Southern analysis. DNA was extracted from tumours 2 and 24 hr following i.p. injection of liposome/DNA complexes and free DNA. DNA (genomic plus plasmid) was isolated, subjected to electrophoresis on an agarose gel and subsequently blotted to a nitrocellulose membrane. The DNA was then probed with $^{32}$P random prime-labeled pInex CAT v2.0 and exposed to phosphoimager for analysis (FIG. 9). DNA isolated from tumours that were administered free plasmid DNA for 2 and 24 hr did not show the presence of any plasmid bands (lanes 2 and 4). This is consistent with the observation that free DNA is not stable under the conditions used. More specifically, levels measured using $^3$H-plasmid following administration of free DNA were likely due to the presence of $^3$H metabolites. DNA isolated from tumours that were treated with liposome/DNA complexes for 2 and 24 hr showed the presence of three plasmid bands (lanes 3 and 5) which have a migration pattern similar to the plasmid control (lane 6). These data indicate that plasmid DNA specifically associated with tumours is intact for up to at least 24 hr following i.p. administration of DODAC/DOPE/pInex CAT v2.0 complexes to B16/BL6 i.p. tumours.

Example 3

This example illustrates the reporter gene expression is mice and young rats using complexes prepared as described above.

3.1 Reporter Gene Expression in Mice and Young Rats.

Female ICR mice (3–4 weeks old, weighing approximately 20 g) and young male Wistar rats (14 days old, weighing approximately 20 g) were used in these studies. Each animal received by tail vein injection, 200 μL of the cationic liposome-plasmid complexes containing 30 μg pCMVlue and 550 nmoles DODAC:DOPE (1:1) formulated at 4° C. The animals were treated in groups of four and control animals received PBS or free plasmid DNA. After 6 h or at time indicated, the animals were sacrificed and their lung, liver and spleen were removed. The tissues were frozen in liquid nitrogen immediately and stored at −70° C. for reporter gene expression analysis.

3.2 Measurement of Luciferase Activity

The weighed tissues were homogenised in 1 mL of luciferase cell lysis buffer using a Fast-prep machine (Savant BIO 101). The liver samples were further diluted with one mL of lysis buffer. All tissue homogenates were subject to three freeze-thaw cycles (5 min at liquid nitrogen temperature followed by 5 min at 37° C.) and centrifuged for 10 min at 14,000 rpm in a refrigerated micro centrifuge at 4° C. (Beckman CS 15R). The supernatants were removed and stored at −70° C. until assayed for luciferase activity. Luciferase activity was determined using a luminometer (Dynex ML 3000) and a commercial Luciferase assay kit (Promega). One hundred microliters of reconstituted luciferase substrate was added to 20 μL of tissue extract in the wells of a microtitre plate using the injection system of the luminometer. Peak light emission was measured for 10 sec at 25° C. The relative light units of each sample were converted to luciferase concentration from a standard curve established by adding known amount of luciferase to the tissue extracts of corresponding organs from control animals. Each sample was assayed in triplicate and the level of reporter gene expression was expressed as the amount of luciferase measured per gram of tissue.

3.3 Results

Luciferase expression in mice

Figure 10:
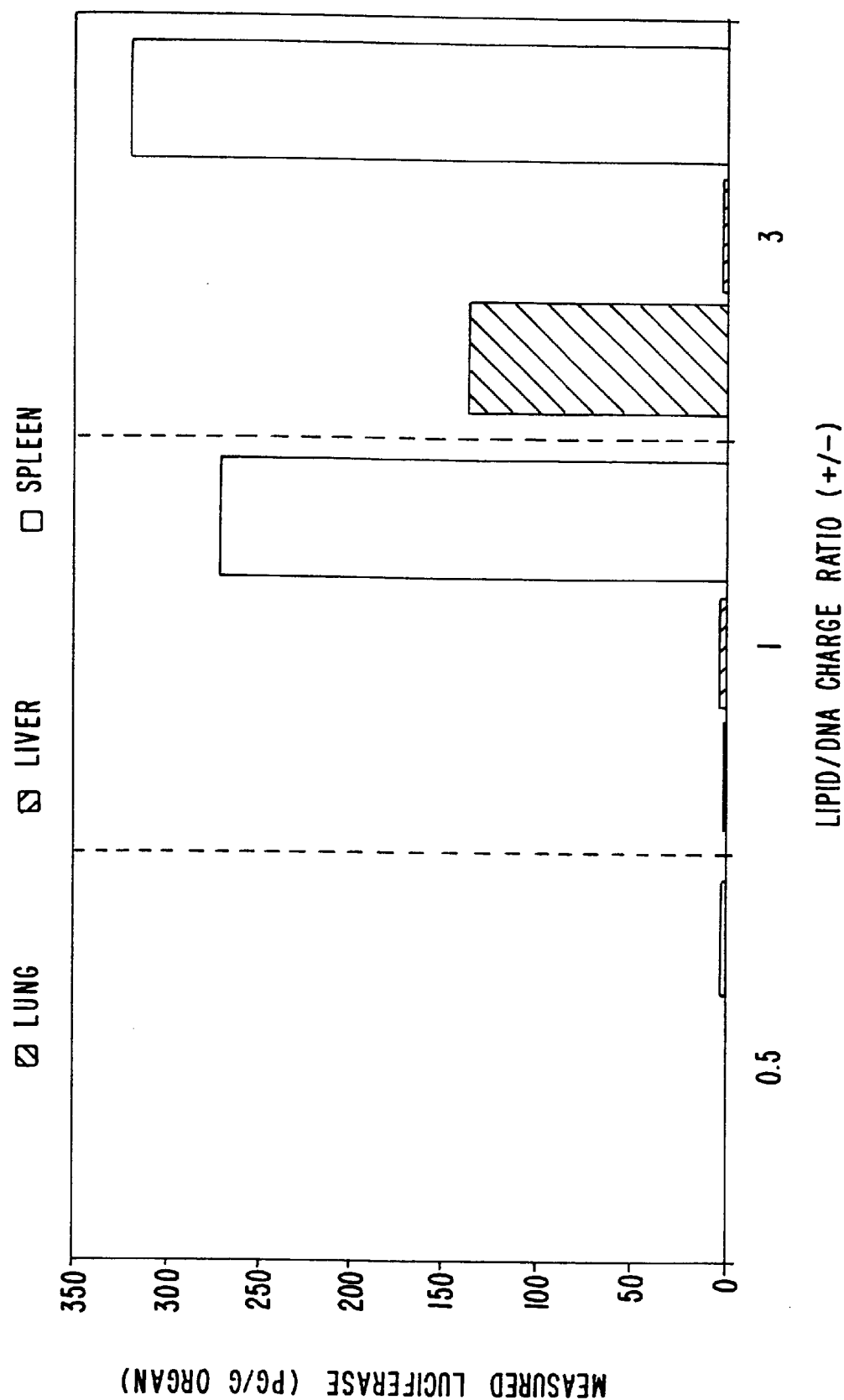
FIG. 10 illustrates the effect of lipid/DNA charge ratios on luciferase expression in mice.

Mice injected intravenously with 30 μg of pCMV plasmid condensed with performed DODAC:DOPE vesicles at 4° C., consistently showed significant levels of luciferase activity in lung and spleen with a low level of activity in liver tissue. As shown in FIG. 10, the level of luciferase expression in the tissues was dependent on the amount of DODAC:DOPE used to condense the DNA. The highest level of luciferase activity was measured in lung, liver and spleen when 550 nmoles DODAC:DOPE were used with 30 μg DNA or at a cationic lipid to DNA charge ratio of 3:1 (+/−). Lower levels of expression was measured in lung, liver and spleen tissues when the DNA was condensed with less lipid at cationic lipid to DNA charge ratio of 1 and 0.5.

Figure 11:
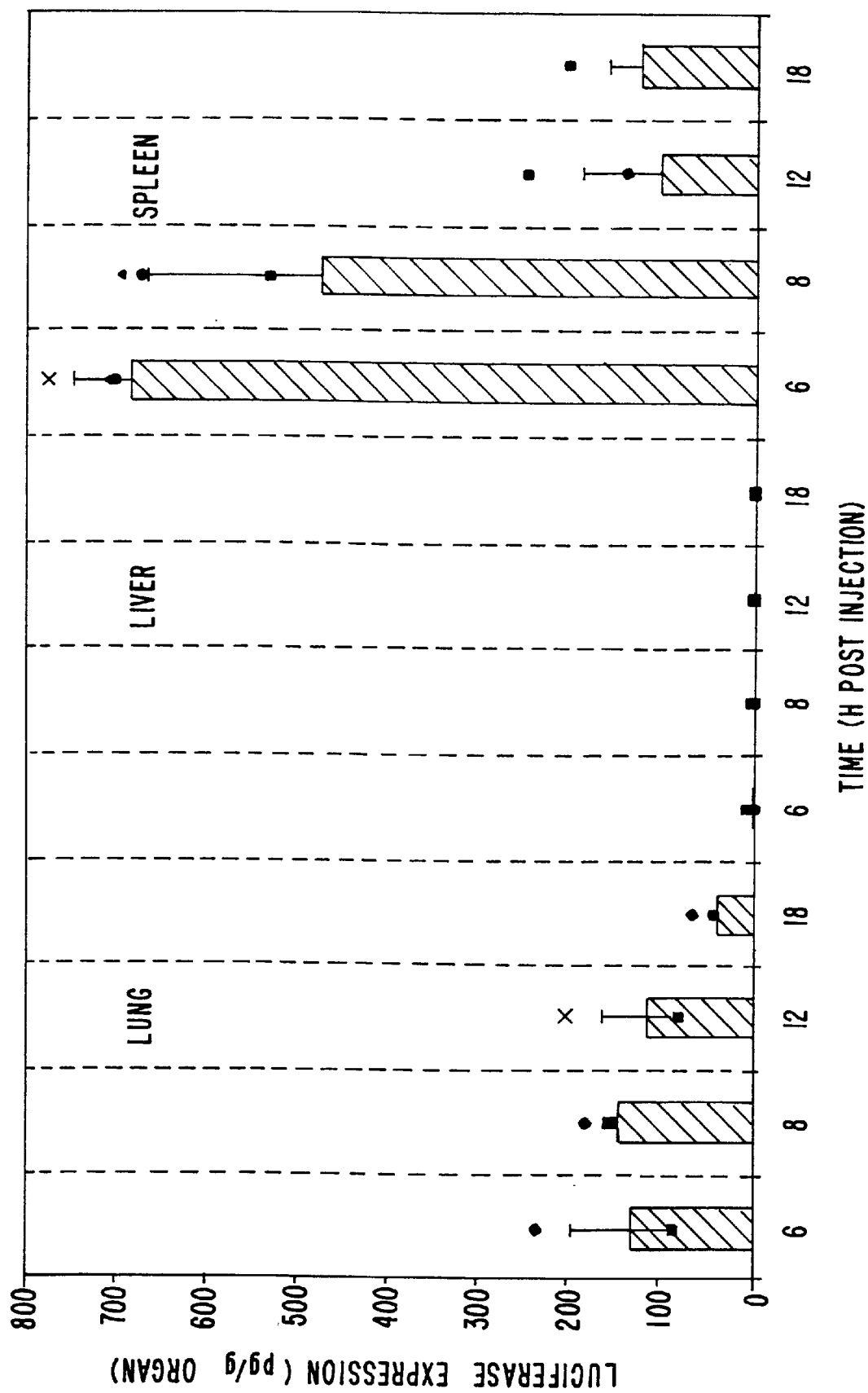
FIG. 11 provides the results of time course experiments for luciferase expression in the lung, liver and spleen of mice treated with cationic liposome-plasmids described in Example 3.

The time course of luciferase expression using DOCDAC:DOPE/pCMVluc formulated at cationic lipid to DNA charge ration of 3:1 is shown in FIG. 11. Maximum luciferase expression in lung and spleen was found at 6 to 8 h following injection of the liposome-plasmid complexes. The expression of luciferase in the tissues decreased subsequently.

Figure 12:
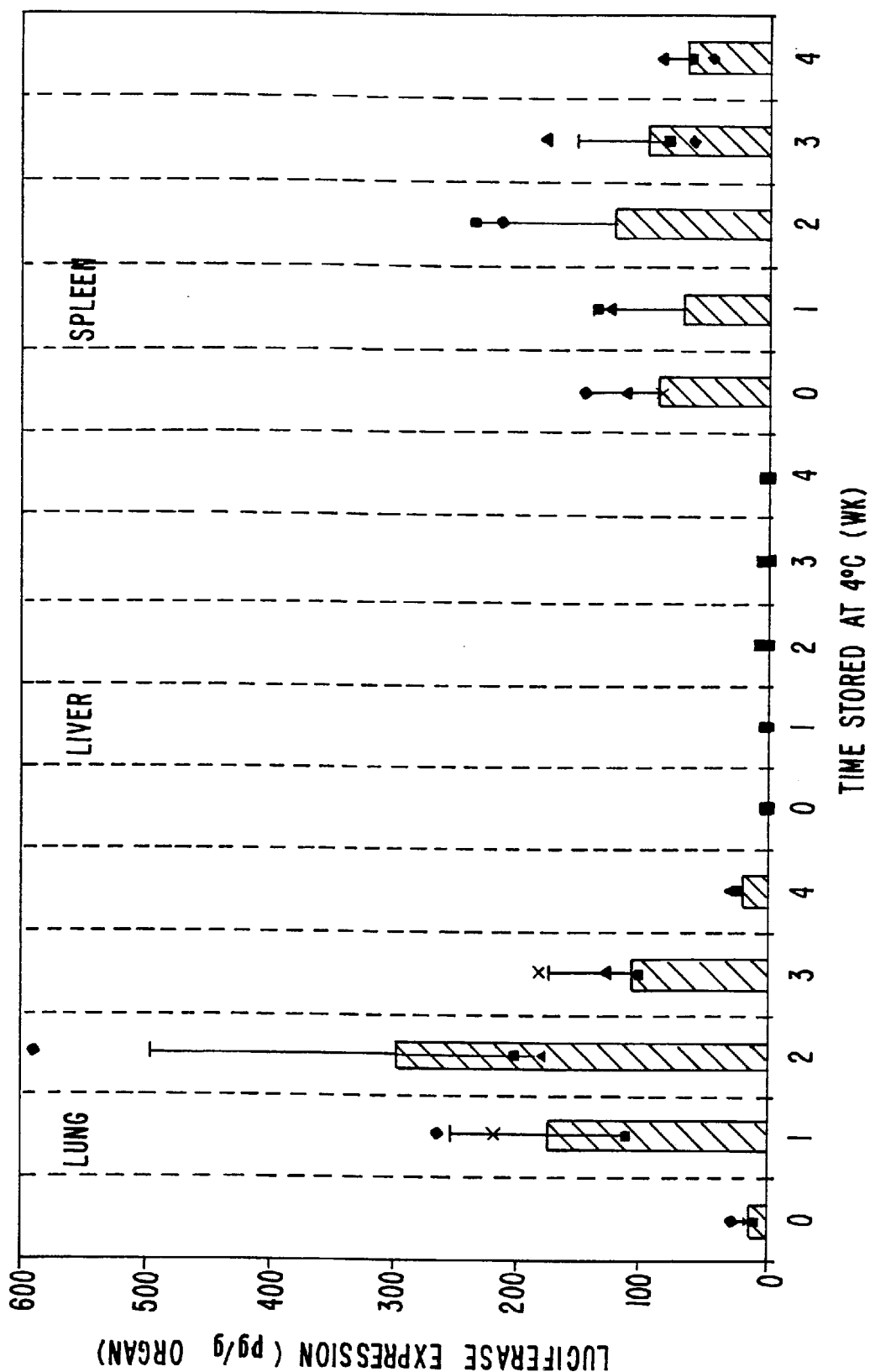
FIG. 12 indicates the levels of luciferase expression in the lung, liver and spleen of mice which can be achieved using complexes following storage of the complexes at 4° C. for up to four weeks.

The cationic liposome-plasmid complexes prepared at 4° C. retained their size distribution and their ability to induce transfection in lung, liver and spleen after intravenous injection in mice. A preparation stored over four weeks at 4° C. gave high transfection activity in lung and spleen after two weeks storage, lower expression was observed with older samples (FIG. 12). This property is important since the corresponding complexes prepared at room temperature had to be used within a shorter period of hours rather than days.

Luciferase expression in young rats

As in the mouse, the intravenous administration of the cationic liposome-plasmid complexes in 14 day old rats, resulted in luciferase activity in lung and spleen of the treated animals. However, consistently high levels of luciferase activity was also detected in the liver of the 14 day old rat.

VII. Conclusion

As discussed above, the present invention provides methods of forming cationic liposome/nucleic acid complexes in which the complexes have a mean diameter of about 200 to about 300 nm are provided. The complexes are formed by combining a first solution of preformed cationic unilamellar liposomes with a mean diameter of from 100 to 150 nm, with a second solution of nucleic acid. Each of the solutions are equilibrated prior to mixing to temperatures of from 0° C. to about 12° C., preferably about 2° C. to about 7° C. The complexes thus formed are surprisingly efficient in transfecting cells, both in vivo and in vitro.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method of preparing cationic liposome/nucleic acid complexes comprising combining a first solution of preformed cationic liposomes with a second solution of nucleic acids, wherein each of said first and second solutions have been pre-equilibrated to temperatures of from 0° C. to 12° C., said preformed cationic liposomes being unilamellar, having a mean diameter of from 100 to 150 nm, and consisting essentially of unsaturated cationic lipids and neutral lipids selected from the group consisting of DOPE, cholesterol and combinations thereof.

2. A method in accordance with claim 1, wherein said first and second solutions have been pre-equilibrated to temperatures of from 2° C. to 7° C.

3. A method in accordance with claim 1, wherein said unsaturated cationic lipid is selected from the group consisting of DODAC, DODAP, DORI, DOSPA, DOTAP, DC-Chol and DMRIE.

4. A method in accordance with claim 1, wherein said unsaturated cationic lipid is selected from the group consisting of DODAC, DODAP and DOTAP.

5. A method in accordance with claim 1, wherein said preformed cationic liposomes consist essentially of DODAC and DOPE in a molar ratio of about 50:50.

6. A method in accordance with claim 1, wherein said first and second solutions are combined and incubated at temperatures of from about 0° C. to about 10° C. for a period of time of from about 10 to about 60 minutes.

7. A method in accordance with claim 1, wherein said nucleic acid is a plasmid.

8. A method in accordance with claim 1, wherein said cationic liposome/nucleic acid complexes have a mean diameter of about 200 to 350 nm.

9. A method in accordance with claim 1, wherein said cationic liposome/nucleic acid complexes have a mean diameter of about 250 to 300 nm.

10. A method for the introduction of nucleic acid into a cell, comprising preparing cationic liposome/nucleic acid complexes according to claim 1 and contacting said complexes with said cell.

11. A method in accordance with claim 10, wherein said cell is a plant cell.

12. A method in accordance with claim 10, wherein said cell is a mammalian cell.

13. A method in accordance with claim 10, wherein said cell is a human cell.

14. A method in accordance with claim 13, wherein said contacting is ex vivo.

15. A method in accordance with claim 13, wherein said contacting is in vivo.

16. A composition prepared according to claim 1.

17. A composition prepared according to claim 6.

* * * * *